United States Patent
McGlothlin et al.

(10) Patent No.: US 6,329,444 B1
(45) Date of Patent: Dec. 11, 2001

(54) DIP-MOLDED MEDICAL DEVICES FROM CIS-1,4-POLYISOPRENE

(75) Inventors: Mark W. McGlothlin; Eric V. Schmid, both of San Diego, CA (US)

(73) Assignee: Apex Medical Technologies, Inc., San Diego, CA (US)

( * ) Notice: Subject to any disclaimer, the term of this patent is extended or adjusted under 35 U.S.C. 154(b) by 0 days.

(21) Appl. No.: 09/172,965

(22) Filed: Oct. 14, 1998

(51) Int. Cl.⁷ .............................. C08L 9/10; C08F 136/08; A61B 19/04; A61M 25/10
(52) U.S. Cl. .......................... 523/105; 522/60; 522/159; 523/300; 524/579; 524/571; 525/332.5; 528/932; 604/96; 2/161.7
(58) Field of Search ................... 525/332.5; 528/932; 523/105, 300; 522/60, 159; 524/579, 571; 604/96; 2/161.7

(56) References Cited

U.S. PATENT DOCUMENTS

| | | | |
|---|---|---|---|
| 2,802,891 | * 8/1957 | Feild et al. ............................. | 524/571 |
| 3,566,874 | * 3/1971 | Shepherd et al. ...................... | 424/81 |
| 3,644,186 | * 2/1972 | Gracia et al. .......................... | |
| 3,961,124 | * 6/1976 | Matton ................................. | 428/250 |
| 3,971,746 | 7/1976 | Hirai et al. ............................ | 524/572 |
| 4,684,672 | * 8/1987 | Buchanan et al. ..................... | |
| 5,357,636 | 10/1994 | Dresdner, Jr. et al. ............... | 2/161.7 |
| 5,399,400 | 3/1995 | Nile et al. ............................. | 523/122 |
| 5,563,241 | * 10/1996 | Beezhold ............................... | |
| 5,691,446 | 11/1997 | Dove .................................... | 528/935 |
| 5,910,567 | * 6/1999 | Tanaka et al. ........................ | |
| 5,997,969 | * 12/1999 | Gardon ................................. | |

FOREIGN PATENT DOCUMENTS

| | | | |
|---|---|---|---|
| 819669 | 9/1959 | (GB) | ................................ |
| 867916 | 5/1961 | (GB) | ................................ |
| 2239247 | 6/1991 | (GB) | ................................ |
| 52086437 | 7/1977 | (JP) | ................................ |

OTHER PUBLICATIONS

Charlesby, The Crosslinking of Rubber by Pile Radiation, *Atomics*, p. 12–20, Jan. 1954.*

* cited by examiner

*Primary Examiner*—Peter Szekely
(74) *Attorney, Agent, or Firm*—Townsend and Townsend and Crew LLP

(57) ABSTRACT

Medical devices of synthetic rubber are prepared from cis-1,4-polyisoprene by dip molding without the use of sulfur containing components. The devices have surprisingly favorable tensile characteristics despite what is known in regard to synthetic cis-1,4-polyisoprene. In addition, the absence of both the proteins present in natural rubber and the sulfur components that are typically used in vulcanization of both natural rubber and cis-1,4-polyisoprene of the prior art renders the devices freely usable without causing the user to suffer Type I or Type IV allergic reactions that typically arise from contact with natural rubber.

34 Claims, No Drawings

DIP-MOLDED MEDICAL DEVICES FROM CIS-1,4-POLYISOPRENE

This invention lies in the field of synthetic rubber articles, particularly those formed by dip-molding. In particular, this invention addresses the use of cis-1,4-polyisoprene in making articles of this type.

BACKGROUND OF THE INVENTION

Natural polyisoprene rubber, which is obtained from *Hevena brasiliensis* rubber trees, has been used extensively as a material of construction for elastomeric dip-molded medical devices and medical device components. Examples of these devices and components are surgical gloves, examination gloves, finger cots, catheter balloons, uterine thermal ablation balloons, catheter cuffs, condoms, contraceptive diaphragms, in-dwelling urinary drainage catheters, and male external urinary drainage catheters.

Dip-molding of natural rubber is performed with either a latex (an aqueous dispersion of rubber particles) or an organic solution of the rubber. Dipping in either the latex or the organic solution is followed by removal of the water or solvent, and the dipping and water or solvent removal are often performed in repeated cycles to achieve a particular film thickness. The film thus formed is then vulcanized to bring the rubber to a fully cured state. In some procedures, prevulcanization is practiced, i.e., vulcanization of the rubber in the dipping medium prior to the dipping step. A film from a prevulcanized dipping medium does not require curing after the dipping step, but instead only drying to remove the water. In further procedures, both prevulcanization and post-curing, i.e., vulcanization both of the dipping solution prior to dipping and of the film after dipping, are used.

In latex dipping, the thickness of the final article is often increased by the use of a coagulant, either as a preliminary coagulant dip or a heat-sensitized coagulant dip. Solvent dipping (the use of an organic solution of the rubber rather than a latex) is performed with any of various solvents, such as benzene, toluene, gasoline, aliphatic hydrocarbons, cycloaliphatic hydrocarbons such as cyclopentane and cyclohexane, and solvent combinations such as hexane and acetone.

Whether a latex or an organic solution is used, articles and devices formed from natural rubber are responsible for a variety of health problems. Some users experience allergic reactions which either begin within minutes of exposure or hours later. Symptoms range from mild reactions such as skin redness, hives or itching, to more serious reactions such as runny nose, itchy eyes, scratchy throat, difficulty in breathing, coughing spells, and wheezing, and in extreme cases, life-threatening shock. When strong reactions are experienced, they are similar in nature to those resulting from bee stings.

Adverse reactions to natural rubber are generally of three types. The first is an irritant dermatitis, which involves skin irritation that is not related to the body's immune response. Although not an allergic reaction, irritant dermatitis can cause breaks in the skin which can provide the components of the rubber, including proteins present in the rubber, with increased access to the body's immune system and lead to a latex allergy. The second type is a delayed cutaneous hypersensitivity, also known as a Type IV allergy. Type IV allergies are generally caused by chemicals such as thiurams that are incorporated into the rubber for vulcanization purposes. This type of reaction is mediated via T-cells, generally occurs within 6 to 48 hours of contact with the rubber article, and is localized to the area of the skin where contact has been made. The third type of reaction is termed an "immediate reaction" and also known as a Type I allergy. Type I allergies are systemic allergic reactions caused by IgE antibodies to the proteins in the natural rubber. Symptoms include hives, rhinitis, conjunctivitis, asthma, and in rare cases anaphylaxis and hypotension. Type I reaction symptoms generally occur within about 30 minutes of exposure.

Thus, the adverse reactions caused by natural rubber are due either to chemicals added to the rubber to promote vulcanization, particularly sulfur-containing chemicals, or to the proteins in the rubber when the rubber is extracted from its natural source. To address the protein-derived reactions, methods of treating natural rubber have been developed to reduce its protein content. One method of achieving this is by a double centrifuge method of processing natural rubber latex—a first centrifuge step removes some of the aqueous phase, and is followed by the addition of water and a second centrifuge step to remove the added water and the protein. This removes some of the protein but not all. Another method has involved the use of enzymes to digest the proteins. This again removes only some of the proteins, not all, and leaves enzymes which are themselves proteins in the latex.

In any event, de-proteinized natural rubber fails to offer the level of performance that is achieved with natural rubber that has not been de-proteinized. Comparative test results are reported by Nakade, S., et al., "Highly Purified Natural Rubber IV. Preparation and Characteristics of Gloves and Condoms," *J. Nat. Rubb. Res.* 12(1): 33–42 (1997). These results show that de-proteinized natural rubber has tensile modulus values and a tear strength level that are lower than those of natural rubber. These deficiencies relative to natural rubber remain even through the use of vulcanization of the rubber by irradiation. A study reported by Mohid, N., et al., "Characterization of NR Latex and Vulcanization," *Nippon Genshiryoku Kenkyusho*, 1990: JAERI-M-89-228, *Proc. Int. Symp. Radiat. Vulcanization Nat. Rubber Latex*, Tokyo/Takasaki, July 1989, pages 157–163, shows that the tensile properties of irradiated de-proteinized rubber are inferior to those of irradiated natural rubber.

Various synthetic elastomers have been used as substitutes for natural rubber. Nitrile and chloroprene synthetic rubber materials, for example, have been used in the manufacture of surgical gloves, medical examination gloves, and dental gloves. These materials do not however match the high resiliency and low tensile set values of natural rubber. Silicone rubber has been used for catheter balloons, but its tensile strength is low relative to natural rubber and must be compensated for by an increased thickness. Polyurethane has also been used as a natural rubber substitute, particularly in dip-molded catheter balloons. Polyurethanes have very high tensile strength but lack the resiliency and low tensile set values of natural rubber. As a result, polyurethanes are not suitable for devices that are required to undergo large degrees of expansion during use and to return to their original configuration upon depressurization. Also, because of their thermoplastic nature, polyurethanes tend to soften and are prone to leakage at elevated temperatures which diminishes their usefulness for devices such as uterine thermal ablation balloons. Gloves have also been prepared from styrene-ethylenelbutylene-styrene tri-block copolymer, but this material suffers from low tensile set values and poor dimensional stability when heated.

The use of formulations based on or derived from cis-1,4-polyisoprene for dip-molded products has been disclosed.

One such disclosure is that of Hirai et al., U.S. Pat, No. 3,971,746, issued Jul. 27, 1976. Hirai et al. disclose the use of a cis-1,4-polyisoprene that has been modified by the introduction of carbonyl groups into the polymer structure, after having recognized that products formed from the unmodified polymer are deformed upon removal from the mold and contains streaks and grooves that render them mechanically deficient. Preiss et al., U.S. Pat. No. 3,215,649, disclose the use of a sulfur-vulcanized cis-1,4-polyisoprene.

To summarize the collective teachings of the prior art, cis-1,4-polyisoprene without the protein that is retained from natural rubber sources is believed to be unsuitable for dip-molded medical devices since products made from deproteinized natural rubber lack the tensile characteristics that are important features of these devices, even those products made from deproteinized rubber that has been crosslinked by irradiation. This expectation is reinforced by molecular weight considerations, the isoprene in natural rubber has a high molecular weight component of from about 1,000,000 amu to about 2,500,000 amu (number average), while synthetic polyisoprene has a considerably lower molecular weight with a number average ranging from about 250,000 amu to about 350,000 amu. A lower molecular weight polymer is expected to have lesser tensile properties, including tensile set values. Synthetic polyisoprene also has a lower degree of branching, lower symmetry, and lower intermolecular forces. All of these characteristics contribute to and affect the tensile properties of the polymer. Furthermore, the prior art distinctly avoids mention of any crosslinking method other than the use of sulfur-containing compounds. Thus, there is no disclosure in the prior art of a dip-molded product of synthetic cis-1,$^4$-polyisoprene that is both protein-free and sulfur-free and that has tensile characteristics that are acceptable for medical devices, particularly those that undergo an elastic expansion during use on the order of 100% (i.e., twice its unexpanded size) or greater.

SUMMARY OF THE INVENTION

It has now been discovered that medical devices formed by dip-molding synthetic cis-1,4-polyisoprene that is both protein-free and sulfur-free have properties that make them suitable as substitutes for devices made of natural rubber, without any of the allergic reactions or other health problems associated with natural rubber. This is contrary to the teachings of the prior art which suggest that synthetic cis-1,4-polyisoprene is inherently inferior to its naturally-occurring counterpart obtained from *Hevena brasiliensis*, and which suggest that sulfur-based vulcanization is needed to achieve the type of performance required in the typical medical uses of these devices. Since synthetic cis-1,4-polyisoprene lacks the proteins present in natural rubber, the Type I allergic ("immediate") reaction, arising either on its own or aggravated by the irritant dermatitis reaction, is avoided entirely. By eliminating the sulfur-containing components, the Type IV allergic reaction is avoided as well, or at least reduced. In addition to eliminating these adverse factors, the resulting product offers unexpectedly good tensile set values (resiliency).

Preferred dip-molded products within the scope of this invention are those that are crosslinked to improve the tensile strength, despite the absence of sulfur in the product. Crosslinking is achievable by such means as high energy radiation, optionally in the presence of a sensitizing agent which may or may not remain in some form in the final product, or by the use of non-sulfur-containing crosslinking agents or promoters. It is surprising that these crosslinking methods, which have not heretofore been disclosed in connection with dip-molded cis-1,4-polyisoprene, are effective in producing a product that meets the tensile and resiliency requirements of these medical devices.

This invention is of particular interest in its application to dip-molded parts that in use will undergo a large degree of dimensional expansion, such as by inflation or other stretching methods. Parts that are typically expanded by about 100% (i.e., twice their original size) or greater, as measured by a linear dimension such as axial length or diameter, or by a nonlinear dimension such as circumference, receive a particular benefit from this invention, since with crosslinking the parts can be expanded and then returned to their original configuration with a tensile set value of less than 5%. The expansion and release can be repeated a multitude of times with little or no distortion of the part. Catheter balloons of various types for various uses are examples of this type of expandable part.

These and other objects, features and advantages of the invention will become apparent and/or better understood from the description that follows.

DETAILED DESCRIPTION OF THE INVENTION AND PREFERRED EMBODIMENTS

The synthetic polymer cis-1,4-polyisoprene is commercially available in the United States from the Goodyear Tire & Rubber Co., Beaumont, Tex., USA, in Western Europe from Shell Nederland Chemie (Royal Dutch/Shell Group), Bernis, Netherlands, and in Japan from Japan Synthetic Rubber Co., Ltd., and Nippon Zeon Co., Ltd. The polymer is produced by polymerizing isoprene over a Ziegler catalyst consisting of isobutylaluminum and titanium tetrachloride, or any of various other catalysts known in the art. Other catalysts include alkali metal catalysts, particularly finely divided lithium metal or organolithium compounds, and other methods include anionic polymerization, cationic polymerization, and free-radical polymerization. The process conditions for each of these methods are known in the industry. For typical synthetic cis-1,4-polyisoprene prior to crosslinking, the weight-average molecular weight of the polymer will generally range from about 750,000 amu to about 950,000 amu, and the number-average molecular weight will generally range from about 250,000 amu to about 350,000 amu.

The formation of articles by dip molding is also well known, and conventional procedures can be followed here as well. Dip molding is achieved by dipping a mandrel, or in general terms, a form whose outer surface has the configuration of the article to be formed, in a liquid medium that contains the liquefied polymer, then withdrawing the form from the liquid to leave a continuous film of the liquid over the surface of the form. The liquid medium may be either a latex (an aqueous emulsion of the polymer in which the polymer is the dispersed phase and water or an aqueous solution is the continuous phase) or a solution of the polymer in an organic solvent. The film is then dried in place on the form (i.e., the solvent or carrier liquid evaporated) and the polymer is cured (vulcanized) after the drying step. The dried and cured film, which is now the article in its final shape and composition, is then stripped from the form.

Additional steps or variations of this basic process include prevulcanization or partial curing of the polymer while still in the dipping medium prior to the dipping step, performing a series of dipping and drying cycles to build up film thickness before removing the article from the dipping form, and including additives in the dipping medium such as cure accelerators, sensitizers or activators, emulsifying agents, crosslinking agents, plasticizers, antioxidants, reinforcing agents, and other materials that are commonly used in the formation of articles from cis-1,4-polyisoprene and other synthetic and natural rubbers. Another variation is the use of coagulant dipping as a separate dipping step to help build up the film thickness. Sulfur, which is a common compounding ingredient for polyisoprene, is avoided in accordance with this invention, as are other common rubber compounding ingredients which include sulfur, such as sulfenamides, thiazoles, thiurams, thiocarbamates. The terms "curing" and "vulcanization" are used herein interchangeably, the term "vulcanization" being used in an analogy with the vulcanization of natural rubber. In the present context, however, "vulcanization" is not intended to include crosslinking with sulfur or any use of sulfur or sulfur-containing compounds.

A latex of cis-1,4-polyisoprene is formed by methods known to those skilled in the art of rubber compounding and processing. These methods include either emulsifying an organic solution of the polymer in an aqueous medium followed by removing the solvent, or liquefying the polymer and combining the liquefied polymer with the aqueous medium under emulsification conditions. Emulsions can be stabilized by various emulsifying agents. Typical emulsifying agents are potassium and sodium salts of rosin acids and higher fatty acids, such as potassium and sodium salts of oleic acid, palmitic acid, stearic acid, lauric acid, myristic acid, arachidic acid, and ricinic acid, as well as sulfates and sulfonates of these acids, such as sodium lauryl sulfate and sodium lauryl sulfonate. Other emulsifying agents are amine salts of hydroxylamines of long-chain fatty acid esters, quaternary ammonium salts such as stearyldimethylbenzylammonium chloride and tridecylbenzenehydroxyethylimidazole chloride, phosphoric esters of higher alcohols such as capryl and octyl alcohol, and monoesters of oleic acid and pentaerythritol such as sorbitan monooleates. The amount of emulsifier may vary, but will generally be from about 0.03% to about 12.0% by weight of the aqueous phase, preferably from about 0.1% to about 3.0% by weight. The relative amounts of aqueous and organic phases in the emulsion may also vary, although in most cases, the volume ratio (organic:aqueous) will range from about 0.5:1 to about 2.0:1, although volume ratios closer to 1:1, such as a range of from about 0.75:1 to about 1.25:1, are preferred. For latices formed in the presence of organic solvents, the solvent is readily removed to leave the solvent-free latex. Conventional means of solvent removal may be used.

If one wishes to concentrate the latex by reducing the amount of water in the latex before dip molding, water can be removed from the latex by conventional methods. A preferred method is ultrafiltration. Ultrafiltration membranes and their use in concentrating latices are disclosed by DelPico, U.S. Pat. No. 4,160,726 (Jul. 10, 1979) and Tanaka et al., U.S. Pat. No. 5,569,740 (Oct. 29, 1996).

The organic solvent which is used either in forming the latex or as the solvent when an organic solution rather than a latex is used as the dipping medium, can be any solvent that is inert to the polyisoprene and is readily removable by evaporation from the dip-molded film. The solvent is preferably an aliphatic hydrocarbon, saturated or unsaturated, and linear, branched, or cyclic, or ethers, esters, alcohols, or amines. Typical solvents are aliphatic hydrocarbons containing 5 to 8 carbon atoms, such as pentane, pentene, hexane, heptane, cyclohexane and cyclopentane, and tetrahydrofuran.

Curing by high energy radiation will achieve crosslinking between the polyisoprene chains by a free radical mechanism. Methods of performing high energy radiation include electron beam radiation and gamma radiation. The radiation can be performed either in the presence or absence of a chemical sensitizer in the liquid medium, although higher energy radiation doses will be needed when no chemical sensitizer is present. When a sensitizer is used, the sensitizer will be one that does not contain sulfur. Such sensitizers are well known. Included among these are certain compounds that contain polymerizable carbon-carbon double bonds. Examples of the latter are 1,3-butylene glycol diacrylate, 1,3-butylene glycol dimethacrylate, 1,6hexanediol diacrylate, neopentyl glycol diacrylate, neopentyl glycol dimethacrylate, ethyl acrylate, n-butyl acrylate, n-hexyl acrylate, and 2-ethylhexyl acrylate. Still further examples are peroxide compounds. Examples are dicumyl peroxide, 2,5-dimethyl-2,5-di(t-butylperoxy)hexane, 2,5-dimnethyl-2,5-di(t-butylperoxy)hexyne, 2,5dimethyl-2,5-di(t-benzoylperoxy)hexane, 2,2'-bis(t-butylperoxy)-diisopropylhexane, 1,1-bis(t-butylperoxy)-3,3,5-trimethyl cyclohexane, n-butyl 4,4-bis(t-butylperoxy)valerate, t-butyl perbenzoate, and benzoyl peroxide. Peroxide compounds are also useful as crosslinking agents apart from radiation, as explained below.

The appropriate radiation dosage will be one that will achieve the desired degree of crosslinking and hence the desired physical characteristics in the final product, and yet will not cause chain scission to the extent of adversely affecting those physical characteristics, Within these considerations, the appropriate dosage will be readily determined by trial and error. In most cases, when no sensitizer is used, best results will be obtained when the dosage is within the range of about 20 megarads to about 40 megarads, and preferably approximately 25 megarads. When a sensitizer, such as n-butyl acrylate for example, is used with gamma radiation, a preferred dosage range is from about 1 megarad to about 5 megarads. When a sensitizer is used with electron beam radiation, a preferred dosage range is from about 10 megarads to about 20 megarads.

Electron beam radiation is applied by known methods. Accelerators used in the generation of the beam typically run at a power within the range of 200 KeV (200,000 electron volts) to 3 MeV (3 million electron volts) and a current of 25–200 mA. Gamma radiation is likewise applied by known methods, notably from radioactive nuclei such as $^{60}$Co and $^{137}$Cs, although $^{210}$Po and $^{226}$Ra are also sources of gamma radiation.

Crosslinking without either sulfur or radiation can be achieved by the use of various non-sulfur-containing chemical crosslinking agents, notably peroxide compounds, hydroxy compounds, diamino compounds and other difunctional crosslinking agents. Examples of peroxide compounds are listed above. Examples of hydroxy compounds are p-quinone dioxime, methylolphenol-formaldehyde resin, brominated and alkylphenol-formaldehyde resin. Examples of diamino compounds are hexamethylenediamine carbamate, N,N'-dicimnmamylidene-1,6-hexanediamine, 4,4'-methylenebis(cyclohexylamine)carbamate, 4,4'-methylenedianiline. Examples of other agents are 1,3-bis(ditraconimidomethyl)- benzene and N,N'-meta-phenylenebismaleimide. Peroxide compounds are preferred, with particular preference for dicumyl peroxide and 2,5-dimethyl-2,5-di(t-butylperoxy)hexane. Typically, an organic peroxide is dissolved in an organic solvent such as toluene, and the resulting solution is added to the polyisoprene prior to dip molding. When a peroxide is used, oxygen gas should be excluded from the system during curing, since the antioxidants typically added to polyisoprene may be rendered ineffective by the peroxide.

Curing with a peroxide compound generally entails the immersion of the polymer in a molten salt bath. Salt combinations for this purpose are commercially available. One example is QUICK CURE 275, a product of Hubbard Hall Inc., Inman, S.C., USA, whose main components are potassium nitrate (approximately 50% by weight), sodium nitrite (approximately 30% by weight), and sodium nitrate (less than 10% by weight). Other salt combinations and commercial products will be readily apparent to those familiar with the use of peroxide curing systems.

The amount of crosslinking agent used will be readily apparent to those familiar with the use of these agents, and the optimal amount for any particular system may vary in accordance with the choice of other components in the system and the conditions of operation. In most cases, best results will be obtained with amounts ranging from about 0.1 to about 10 parts by weight per 100 parts by weight of the polyisoprene, preferably from about 0.3 to about 3 parts by weight.

A desired feature of the typical finished medical device or part in accordance with this invention is a low tensile set value. The tensile set value generally depends on the degree of crosslinking and is a measure of the ability of the device or part, after having been stretched either by inflation or by an externally applied force, to return to its original dimensions upon deflation or removal of the applied force. The tensile set value for a particular material can be determined, for example, by placing two reference marks on a strip of the material and noting the distance between them along the strip, stretching the strip to a preselected degree, for example by increasing its elongation to 90% of its expected ultimate elongation, holding the stretch for a preselected period of time, for example one minute, then releasing the strip and allowing it to return to its relaxed length and remeasuring the distance between the two reference marks. The tensile set value is then determined by comparing the measurements before and after the stretch, subtracting one from the other, and dividing the difference by the measurement taken before the stretch. In this invention, using a stretch of 90% of its expected ultimate elongation and a holding time of one minute, the preferred tensile set value is less than 5%.

This invention is applicable to a wide range of medical devices and parts. These include, but are not limited to, surgical gloves, examination gloves, finger cots, catheter balloons, uterine thermal ablation balloons, catheter cuffs, condoms, contraceptive diaphragms, in-dwelling urinary drainage catheters, and male external urinary drainage catheters. Other examples will be readily apparent to those in the medical field. In certain embodiments, this invention is particularly well suited for devices whose use typically involves an expansion by pressurization to the extent that a dimension such as a length or circumference is increased by at least 100%, i.e., at least doubled. Many parts of this description are balloons. Examples are the balloons in right heart monitoring balloon catheters such as cardiac output thermal dilution catheters, the balloons in embolectomy catheters used for the retrieval of blot clots in blood vessels, and the balloons in urinary drainage catheters.

The following examples are offered for purposes of illustration and are not intended to limit the scope of the invention.

EXAMPLE 1

This example illustrates the formation of synthetic polyisoprene films by dip-molding with a latex that is prevulcanized by irradiation.

The polyisoprene used in this preparation was NATSYN 2200 cis-1,4-polyisoprene, a product of The Goodyear Tire & Rubber Company, Chemical Division, Akron, Ohio, USA. To prepare a solution of the polyisoprene in n-hexane, a 35-L stainless steel mixing vessel fitted with a laboratory mixer with stainless steel shaft and disintegrator mixing head was used. n-Hexane (20 L) was added to the vessel and the mixer was run at 1700 rpm. The polyisoprene (1983 g) was cut into small pieces of about 10 g each and added slowly to the mixing vessel. Mixing was continued for four hours, during which time most of the polyisoprene dissolved. A further 5 L of n-hexane were then added to lower the viscosity of the solution and mixing was continued for an additional four hours within which time the polyisoprene fully dissolved.

An emulsion of the solution was prepared in a high-shear rotor/stator mixer/emulsifier (Model 100LC, Charles Ross & Son Company, Hauppage, N.Y., USA) by charging the vessel with purified water (600 g) and DRESINATE 214 anionic surfactant (7 g, a potassium salt of a modified rosin, obtained from Hercules Inc., Wilmington, Del., USA). The contents of the vessel were mixed until all the surfactant had dissolved. The polyisoprene-n-hexane solution (600 g) was then added to the vessel, and mixing was continued at 10,000 rpm for five minutes. The resulting emulsion was allowed to stand for approximately one hour, after which time a small amount of non-emulsified material was removed. This procedure was repeated several times until the quantity of emulsion amounted to several liters.

To convert the emulsion to a latex, one liter of the emulsion was placed in a controlled temperature bath and slowly heated to boil off the hexane. The heating rate was sufficiently controlled to prevent overflow of foam developed by the boiling hexane, and within two hours (at a final temperature of 87° C.) all hexane had been removed, leaving a dilute latex. This procedure was repeated several times until the quantity of dilute latex amounted to several liters. The dilute latex was concentrated to approximately 46% solids by ultrafiltration, using ultrafiltration cartridge Model UFP-500-C4A from A/G Technology Corporation, Needham, Mass., USA.

Once concentrated, the latex was prevulcanized using electron beam radiation. This was accomplished by placing samples of the latex in sealable plastic containers that were 3 cm in depth. Irradiation was performed at Nicolet Electron Services, San Diego, Calif., USA. Samples were initially irradiated at doses of 2.5, 5.0, 7.5, and 10 megarads, then re-irradiated to total doses of 25, 37.5, and 50 megarads.

A coagulant solution was prepared by combining 120 g of ethyl alcohol, 80 g of calcium nitrate, and 0.2 g of sodium lauryl sulfate. A glass tube was dipped into the coagulant solution, and the film thus formed on the tube surface was dried with a hair dryer. The tube was then dipped into the prevulcanized latex and withdrawn after several seconds. This produced a wet film on the tube surface, which was then dried in a forced-air oven for 15 minutes at 70° C. The film was allowed to cool to room temperature, then stripped from the tube. The film was then leached in purified water at 70° C. for two hours, the re-dried for at 70° C. for 15 minutes.

Tensile testing of the films was performed by Akron Rubber Development Laboratory, Inc., Akron, Ohio, USA, using Die C dumbbells at a pull rate of 20 inches per minute. The test results are listed in Table I:

TABLE I

Tensile Test Results

| Irradiation Dose (megarads) | Tensile Strength (MPa) | Elongation at Break (%) |
|---|---|---|
| 25.0 | 7.3 | 1070 |
| 37.5 | 5.9 | 864 |
| 50.0 | 4.9 | 720 |

The test results shown in Table I indicate that all films had favorable tensile characteristics.

Determinations of tensile set values were performed on films prepared from latex materials that were mixtures of equal parts by volume of a latex subjected to a dosage of 25 megarads and a latex subjected to a dosage of 37.5 megarads. Five films were cast from this mixture in the manner described above. Each film was stretched to a length nine times it original length, held for one minute, then relaxed and the lengths remeasured. In each case, all showed less than 2% tensile set, i.e., less than 2% additional length in the relaxed state due to the stretching.

EXAMPLE 2

This example illustrates the formation of synthetic polyisoprene films by dip-molding with a latex that has been compounded with dicumyl peroxide.

A dispersion of dicumyl peroxide was prepared by mixing together the following under high shear: 100 parts by weight dicumyl peroxide, 35 parts by weight toluene, 5.6 parts by weight octanoic acid, 101 parts by weight water, and 2.6 parts by weight 30% aqueous KOH. The resulting dispersion (40 g) was mixed into 1,000 g of the synthetic polyisoprene latex prepared in Example 1. The materials were allowed to stand for a period of time to allow the peroxide to penetrate the latex particles.

A glass tube was first coated with a film of coagulant in the manner described in Example 1, then dipped in the peroxide-containing latex, air dried and cured. Curing was accomplished by immersing the tube in a 180° C. salt bath (QUICK CURE 275, referenced above) for a period of two minutes. The tube was then rinsed in cool water, and the cured film was stripped from the tube.

Measurements of the tensile modulus were taken. The 100% tensile modulus was 93 psi, the 300% tensile modulus was 140 psi, and the 500% tensile modulus was 316 psi. A determination of the tensile set value was made by stretching the film to eight times its original length, holding it thus stretched for one minute, allowing it to relax to its unstretched state, and measuring its length after relaxation. The measurement revealed a tensile set value of less than 1%.

EXAMPLE 3

This example is a further illustration of the formation of synthetic polyisoprene films by dip-molding with a latex compounded with dicumyl peroxide.

A solution was prepared by dissolving 21 g of NATSYN 2200 cis-1,4-polyisoprene in 700 g of tetrahydrofuran, using a medium shear mixer with a propeller blade. Dicumyl peroxide (0.63 g) was then mixed in to this solution and immediately dissolved. Bubbles in the solution were allowed to dissipate, and a mandrel form was immersed in the solution, then slowly withdrawn and the resultant film allowed to air-dry for 15 minutes. The dipping and drying were repeated eight times, with final air drying for 1.5 hours. The film was then cured in a molten QUICK CURE 275 salt bath at 180° C. for three minutes, rinsed and allowed to cool to room temperature. Once cool, the film was powdered and removed from the dipping mandrel. A test strip measuring 0.8 inch by 2 inches was cut from the film.

The tensile test results revealed a tensile modulus of 129 psi at 100% elongation, 319 psi at 300% elongation, and 831 psi at 500% elongation. The tensile set value was determined by stretching the strip to six times is original length and holding the stretch for one minute before allowing the strip to relax. The result was a tensile set value of less than 2%.

EXAMPLE 4

This example illustrates the formation of a synthetic polyisoprene catheter balloon by dip-molding from an organic solution of polyisoprene rather than a latex. A peroxide curing system was used.

The solution was prepared by dissolving 40 g of NATSYN 2200 cis-1,4-polyisoprene in 1,000 g of tetrahydrofuran, using a medium shear mixer with a propeller blade. To this solution was added 1.2 g of dicumyl peroxide, which immediately dissolved. Bubbles in the solution were allowed to dissipate, and a catheter balloon-forming mandrel was immersed in the solution, then slowly withdrawn and allowed to air-dry. The mandrel was then reimmersed, withdrawn and dried for a total of nine repetitions to increase the thickness of the film formed over the mandrel surface. After the final dip, the mandrel was dried in a forced air oven for a period of two hours to evaporate essentially all of the residual solvent. The mandrel was then immersed in a molten QUICK CURE 275 salt bath at 180° C. for a period of four minutes. The mandrel was then allowed to cool, then rinsed in cool water.

The balloon thus formed was removed from the mandrel, trimmed to size, and fitted onto a catheter where it was inflated and deflated repeatedly (150 cycles). Very little bagging of the balloon due to tensile set could be observed even after multiple inflation and deflation cycles.

EXAMPLE 5

This example illustrates the formation of a synthetic polyisoprene surgical glove by dip-molding from an organic solution of polyisoprene using a peroxide curing system.

The solution was prepared by dissolving 160 g of NATSYN 2200 cis-1,4-polyisoprene in 4,000 g of tetrahydrofuran, using a medium shear mixer with a propeller blade. To this solution was added 3.2 g of dicumyl peroxide, which immediately dissolved. Bubbles in the solution were allowed to dissipate, and a glove form was immersed in the solution, then slowly withdrawn and allowed to air-dry. During the drying process, the glove form was rotated about both axes to help achieve an even distribution of the dipping solution. A total of six successive dipping and drying cycles were performed. After the sixth dip, the coated glove form was dried in a forced air oven for two hours to evaporate essentially all of the residual solvent. The glove form and its coating were then immersed in a molten QUICK CURE 275 salt bath at 180° C. for ten minutes. The glove form and coating were then allowed to cool, then rinsed in cool water and air dried. Dusting powder was then applied to the now cured glove to prevent sticking, and the glove was stripped from the glove form.

The glove thus formed demonstrated good resiliency and was essentially transparent. The glove was placed in a forced-air oven at 40° C. to allow for the removal of the volatile products resulting from the breakdown of the dicumyl peroxide.

The foregoing is offered primarily for purposes of illustration. It will be readily apparent to those skilled in the art that the materials and their proportions, as well as the operating conditions, procedural steps and other parameters of the inventions described herein may be further modified or substituted in various ways without departing from the spirit and scope of the invention.

We claim:

1. A medical device for use in contact with living human tissue, comprised of synthetic cis-1,4-polyisoprene, said device being both protein-free and sulfur-free, said device formed by dip-molding, and said cis-1,4-polyisoprene crosslinked subsequent to said dip-molding to an extent sufficient to achieve a tensile set value of less than 5%.

2. A medical device in accordance with claim 1 in which said synthetic cis-1,4-polyisoprene is crosslinked by high-energy electron beam radiation.

3. A medical device in accordance with claim 1 in which said synthetic cis-1,4-polyisoprene is crosslinked by high-energy electron beam or gamma radiation in the absence of chemical sensitizing agents.

4. A medical device in accordance with claim 3 in which partial crosslinking is performed by irradiation of said synthetic cis-1,4-polyisoprene prior to said dip-molding.

5. A medical device in accordance with claim 3 in which said crosslinking is performed by irradiation of said synthetic cis-1,4-polyisoprene.

6. A medical device in accordance with claim 3 in which said crosslinking is performed by irradiation of said synthetic cis-1,4-polyisoprene both prior to and subsequent to said dip-molding.

7. A medical device in accordance with claim 3 in which said crosslinking is performed by irradiation at an intensity of from about 20 megarads to about 40 megarads.

8. A medical device in accordance with claim 1 in which said synthetic cis-1,4-polyisoprene is crosslinked by gamma radiation at an intensity of from about 1 megarad to about 5 megarads, in the presence of a sensitizing amount of n-butyl acrylate.

9. A medical device in accordance with claim 1 in which said synthetic cis-1,4-polyisoprene is crosslinked by high-energy electron-beam radiation at an intensity of from about 10 megarads to about 20 megarads, in the presence of a sensitizing amount of n-butyl acrylate.

10. A medical device in accordance with claim 11 in which said synthetic cis-1,4-polyisoprene is crosslinked by high-energy electron-beam or gamma radiation in the presence of a sensitizing amount of a peroxide compound.

11. A medical device in accordance with claim 1 in which said synthetic cis-1,4-polyisoprene is crosslinked by a peroxide crosslinking agent during immersion in a molten salt bath.

12. A medical device in accordance with claim 11 in which said peroxide crosslinking agent is dicumyl peroxide.

13. A medical device in accordance with claim 11 in which said peroxide crosslinking agent is 2,5-dimethyl-2,5-di(t-butyl-peroxy)hexane.

14. A medical device in accordance with claim 1 in which said dip-molding comprises dipping a mold into a latex of said synthetic cis-1,4-polyisoprene.

15. A medical device in accordance with claim 1 in which said synthetic cis-1,4-polyisoprene is crosslinked by high-energy electron beam or gamma radiation subsequent to dip-molding, in the presence of a chemical sensitizing agent, and said dip-molding comprises dipping a mold into a latex of said synthetic cis-1,4-polyisoprene containing said chemical sensitizing agent.

16. A medical device in accordance with claim 1 in which said dip-molding comprises dipping a mold into a hydrocarbon solvent in which said synthetic cis-1,4-polyisoprene is dissolved or dispersed.

17. A medical device in accordance with claim 16 in which said medical device is a surgical medical examination glove.

18. A medical device designed for elastic expansion by inflation during use to increase a dimension of said device by at least about 100% and to substantially return said linear dimension to its uninflated length upon deflation, said device comprised of synthetic cis-1,4-polyisoprene formed by dip-molding and crosslinked subsequent to said dip-molding to an extent sufficient to achieve a tensile set value of less than 5%.

19. A medical device in accordance with claim 18 in which said medical device is an elastomeric catheter balloon.

20. A medical device in accordance with claim 18 crosslinked to an extent sufficient to achieve a tensile set value of less than 5%.

21. A surgical or medical examination glove comprised of synthetic cis-1,4-polyisoprene that is both protein-free and sulfur-free, and that has been formed by dip-molding from a latex of synthetic cis-1,4-polyisoprene and cured with a peroxide curing agent subsequent to dip-molding during immersion in a molten salt bath.

22. A surgical or medical examination glove comprised of synthetic cis-1,4-polyisoprene that is both protein-free and sulfur-free, and that has been formed by dip-molding from a latex of synthetic cis-1,4-polyisoprene, said latex having been partially cured by radiation prior to said dip-molding in the substantial absence of chemical crosslinking radiation agents and further cured by radiation subsequent to dip-molding.

23. A glove in accordance with claim 22 in which said partial curing prior to said dip-molding is by electron beam radiation.

24. A glove in accordance with claim 22 in which said partial curing prior to said dip-molding is by gamma radiation.

25. A surgical or medical examination glove comprised of synthetic cis-1,4-polyisoprene that is both protein-free and sulfur-free, and that has been formed by dip-molding from a latex of synthetic cis-1,4-polyisoprene, said latex having been partially cured by radiation prior to said dip-molding in the presence of a sensitizing amount of a chemical radiation sensitizing agent and further cured by radiation subsequent to dip-molding.

26. A glove in accordance with claim 25 in which said chemical radiation sensitizing agent is an organic peroxide.

27. A glove in accordance with claim 26 in which said organic peroxide is dicumyl peroxide.

28. A glove in accordance with claim 26 in which said organic peroxide is 2,5-dimethyl-2,5-di(t-butyl-peroxy) hexane.

29. A surgical or medical examination glove comprised of synthetic cis-1,4-polyisoprene that is both protein-free and sulfur-free, and that has been formed by dip-molding from a latex of synthetic cis-1,4-polyisoprene, said latex having been partially cured by a peroxide curing agent prior to said dip-molding and further cured by said peroxide curing agent subsequent to dip-molding.

30. A medical device for use in contact with living human tissue, said device being comprised of synthetic cis-1,4- polyisoprene and free of protein and of sulfur from crosslinking agents or promoters, said device being formed by dip-molding, crosslinked by a peroxide crosslinking agent, and treated by immersion in a molten salt bath subsequent to dip-molding.

31. A medical device in accordance with claim 30 in which said peroxide crosslinking agent is dicumyl peroxide.

32. A medical device in accordance with claim 30 in which said peroxide crosslinking agent is 2,5-dimethyl-2,5-di(t-butyl-peroxy)hexane.

33. A medical device in accordance with claim 30 in which said dip-molding comprises dipping a mold in to a latex of said synthetic cis-1,4-polyisoprene.

34. A medical device in accordance with claim 30 in which said dip-molding comprises dipping a mold into a hydrocarbon solvent in which said synthetic cis-1,4-isoprene is dissolved or dispersed.

\* \* \* \* \*